(12) United States Patent
Gerez

(10) Patent No.: US 10,345,194 B2
(45) Date of Patent: Jul. 9, 2019

(54) DETECTION DEVICE FOR INITIATING FAILURES OF A MECHANICAL SYSTEM

(71) Applicant: SAFRAN AIRCRAFT ENGINES, Paris (FR)

(72) Inventor: Valerio Gerez, Yerres (FR)

(73) Assignee: SAFRAN AIRCRAFT ENGINES, Paris (FR)

( * ) Notice: Subject to any disclaimer, the term of this patent is extended or adjusted under 35 U.S.C. 154(b) by 1073 days.

(21) Appl. No.: 14/575,096

(22) Filed: Dec. 18, 2014

(65) Prior Publication Data

US 2015/0177101 A1    Jun. 25, 2015

(30) Foreign Application Priority Data

Dec. 20, 2013  (FR) ...................................... 13 63177

(51) Int. Cl.
| | |
|---|---|
| *G01M 15/00* | (2006.01) |
| *G01H 1/00* | (2006.01) |
| *G01M 15/12* | (2006.01) |
| *G01M 15/14* | (2006.01) |
| *G01N 29/04* | (2006.01) |

(52) U.S. Cl.
CPC ............ *G01M 15/00* (2013.01); *G01H 1/003* (2013.01); *G01M 15/12* (2013.01); *G01M 15/14* (2013.01); *G01N 29/04* (2013.01)

(58) Field of Classification Search
CPC ...... G01M 15/00; G01M 15/12; G01M 15/14; G01H 1/003; G01N 29/04
USPC .......................................................... 702/35
See application file for complete search history.

(56) References Cited

U.S. PATENT DOCUMENTS

| | | |
|---|---|---|
| 2006/0122809 A1 | 6/2006 | Clarke et al. |
| 2012/0148400 A1 | 6/2012 | Gerez et al. |
| 2013/0211768 A1 | 8/2013 | Gerez et al. |

FOREIGN PATENT DOCUMENTS

| | | | |
|---|---|---|---|
| DE | 10 2007 039 699 A1 | 2/2009 | |
| EP | 1 840 361 A1 | 10/2007 | |
| FR | 2 965 915 A1 | 4/2012 | |
| FR | 2 965 915 A1 | 4/2012 | |

(Continued)

OTHER PUBLICATIONS

French Preliminary Search Report dated Sep. 8, 2014, in French Application No. 13 63177 filed Dec. 20, 2013 (with English Translation of Categories of Cited Documents).

*Primary Examiner* — Michael P Nghiem
*Assistant Examiner* — Dacthang P Ngo
(74) *Attorney, Agent, or Firm* — Oblon, McClelland, Maier & Neustadt, L.L.P.

(57) ABSTRACT

A method and a device for detection of initiating failures in a mechanical system. The device includes an acquisition circuit to acquire packets of endogenic and exogenic time signals corresponding to measurements of endogenic and exogenic parameters specific to the mechanical system respectively, at successive instants, and a chopping circuit to chop a passband of the endogenic signal packets into a determined set of frequency sub-bands, at each instant in the successive instants. The device further includes a calculation circuit to determine a corresponding estimating signal for each frequency sub-band at each instant in the successive instants; and a detection circuit to receive each estimating signal and the corresponding exogenic signal packets during the successive instants, and to detect any deviation in each estimating signal representing initiating failures of the machine in iso-context.

9 Claims, 3 Drawing Sheets

(56) References Cited

FOREIGN PATENT DOCUMENTS

| | | |
|---|---|---|
| WO | WO 2004/040251 A1 | 5/2004 |
| WO | WO 2013/038091 A1 | 3/2013 |

DETECTION DEVICE FOR INITIATING FAILURES OF A MECHANICAL SYSTEM

TECHNICAL FIELD

This invention relates to the field of devices for detection of initiating failures of a mechanical system and particularly of an engine or engine component on a test bench.

STATE OF PRIOR ART

A machine such as an engine makes use of very sophisticated technologies and is systematically tested on a test bench.

In general, test bench operators test the machine under extreme operating conditions and often need to test new equipment. Furthermore, operation or the operating procedure of the mechanical system may be very random and unpredictable. This may lead to safety problems and serious risks of damage to the machine and the bench that is very expensive, which can cause delays in the development of the machine.

At the present time, there are devices for checking and monitoring operation of the test bench to prevent damage to the machine or the test bench. However, these devices are fairly complex and require recording of a very large number of measurements and a high cost in calculation time to process this very large number of measurements.

Consequently, the purpose of this invention is to disclose a simple device for fast detection of initiating failures of a mechanical system such as an engine on a test bench capable of precisely detecting the occurrence of initiating failures in the mechanical system.

PRESENTATION OF THE INVENTION

This invention is defined by a device for detection of initiating failures in a mechanical system comprising:
- acquisition means configured to acquire packets of endogenic and exogenic time signals corresponding to measurements of endogenic and exogenic parameters specific to said mechanical system respectively, at successive instants,
- chopping means configured to chop a passband of said endogenic signal packets into a determined set of frequency sub-bands, at each instant in said successive instants,
- calculation means configured to determine a corresponding estimating signal for each frequency sub-band at each instant in said successive instants, and
- detection means configured to receive each estimating signal and the corresponding exogenic signal packets during said successive instants, and to detect any deviation in each estimating signal representing initiating failures of said machine in iso-context.

Thus, the device can be used to identify the sudden or progressive appearance of a change in the vibration or acoustic spectrum (for example a new, sudden noise or with a crescendo) announcing or revealing a developing failure (for example such as scaling of a bearing or a gear), within the ambient noise of a mechanical system.

Advantageously, said estimating signal is an RMS (Root Mean Square) signal, in each frequency sub-band.

This makes it easy to monitor the change in the level of the RMS value in order to detect any significant deviation from a "normal" known by definition. This "normal" is a set of parameter values defining a standard behavior of the mechanical system and for example stored in a database.

Advantageously, said acquisition means comprise:
- reception means to receive an endogenic signal at each instant in said successive instants, representing measurements of endogenic parameters and an exogenic signal representing measurements of exogenic parameters, said exogenic signal being acquired at a predetermined low frequency and said endogenic signal being acquired at a predetermined high frequency, and
- reading means to chop said endogenic and exogenic signals in time into said endogenic and exogenic time signal packets respectively.

This can be used to acquire analog endogenic and exogenic signals, to convert them into digital signals and to chop them into several files to facilitate processing.

Advantageously, said chopping means comprise a determined set of filters adapted to chop the passband of endogenic signal packets into a set of consecutive frequency sub-bands.

This facilitates detection of any change in an unprocessed signal by chopping it into a plurality of signals in a plurality of consecutive frequency sub-bands.

Advantageously, the device comprises windowing means to under-sample each estimating signal corresponding to each frequency sub-band at the same sampling frequency as said low frequency of exogenic time signals.

This allows the detection means to receive the endogenic parameters and exogenic parameters corresponding to the same frequency.

Advantageously, the detection means are configured to calculate a probability of deviation conditioned by the corresponding exogenic time signals for each estimating signal, said estimating signal and said corresponding exogenic signals being sampled at the same said low frequency.

Advantageously, said endogenic measurements comprise vibration measurements and/or acoustic measurements, and said exogenic measurements comprise context measurements among the following measurements: pressure measurements, temperature, torque and speed measurements of at least part of the elements of said mechanical system.

Advantageously, said mechanical system is a machine or an assembly composed of a machine or part of a machine on a test bench.

Advantageously, said machine is an aircraft engine or a component of an aircraft engine.

The invention also applies to a method of detecting initiating failures in a mechanical system comprising the following steps:
- acquire endogenic and exogenic time signal packets at successive instants corresponding to endogenic parameter measurements and exogenic parameter measurements specific to said mechanical system respectively,
- chop a passband of said endogenic signal packets into a determined set of frequency sub-bands at each instant in said successive instants,
- determine an estimating signal corresponding to each frequency sub-band at each instant in said successive instants,
- receive each estimating signal and the corresponding exogenic signal packets during said successive instants, and
- detect any deviation in each estimating signal representative of initiating failures of said machine, in iso-context.

The invention also aims at a computer program comprising code instructions for implementation of the detection method according to the above characteristics when it is executed by a computer.

DETAILED PRESENTATION OF PARTICULAR EMBODIMENTS

The basic idea of the invention is to monitor a vibration or acoustic signal emitted by a machine or by a system comprising a machine and a test bench in time, in order to detect any difference announcing an anomaly.

For conciseness, in the following we will use the expression "mechanical system" to denote a machine (for example an engine and particularly an aircraft engine) or a component of a machine or a test bench comprising a machine or a component of a machine.

Figure 1:
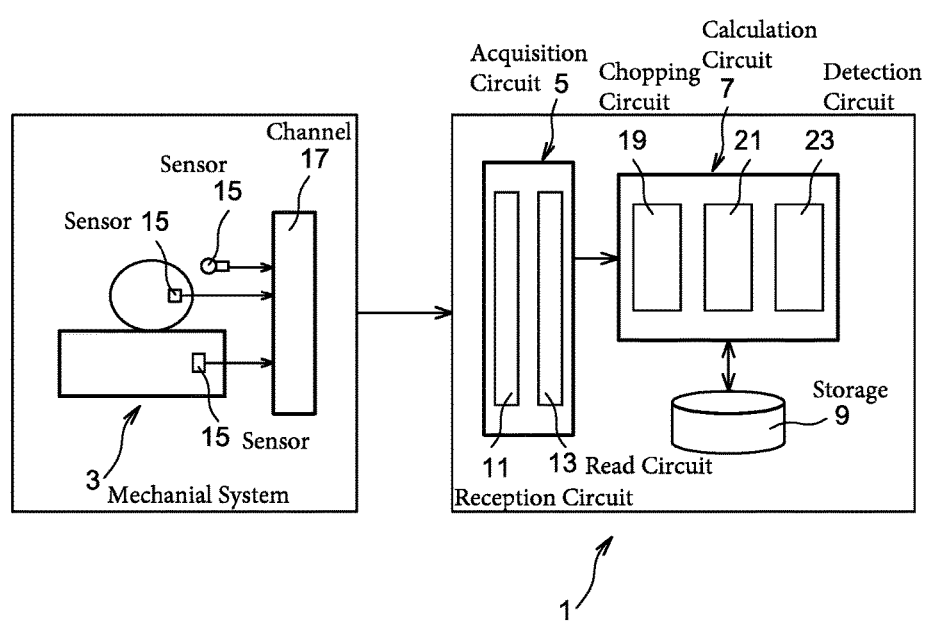
FIG. 1 diagrammatically shows a device for detection of initiating failures in a mechanical system according to the invention.

FIG. 1 diagrammatically shows a detection device 1 to detect initiating failures of a mechanical system 3 according to the invention. This device 1 comprises data acquisition means 5 and data processing means 7 such as a computer for execution of a computer program. This computer program contains program code instructions, stored in computer storage means 9 and designed to implement a method according to the invention for the detection of initiating failures.

The acquisition means 5 comprise reception means 11 and read means 13. These means are configured to acquire a wide passband of endogenic and exogenic time signal packets at successive instants (for example at regular instants), corresponding to measurements of endogenic parameters and exogenic parameters specific to the mechanical system 3, respectively.

Several sensors 15 are used to acquire measurements on the mechanical system 3. These measurements are received by reception means 5 through communication channels 17 at constant frequencies. Measurements related to endogenic parameters are saved by microphones and/or accelerometers and are recorded at high frequency (of the order of 50 kHz). Exogenic measurements are recorded at low frequency (about 1 Hz to 10 Hz). An exogenic parameter is a contextual parameter that represents the context (in other words an operating procedure or operating conditions) of the mechanical system. On the other hand, an endogenic parameter is an observable parameter to be monitored and analyzed as a function of its observation context to detect an anomaly or an initiating failure. An endogenic or exogenic parameter may be identified making use of criteria determined by expertise. For example, measurements of exogenic parameters include pressure, temperature, torque, speed measurements, etc., of at least part of the devices in the mechanical system. On the other hand, measurements of endogenic parameters comprise vibration measurements, acoustic waves, energies, unbalanced masses, etc. Obviously, information about an acoustic wave is not the same in all contexts.

It should be noted that the number of measurements recorded on the mechanical system 3 may be high. In this case, it is advantageous to not process all measurements simultaneously by subdividing the set of measurements into subassemblies of measurements related to different elements or devices of the mechanical system 3 according to criteria set up by expertise.

For example, for a mechanical system 3 composed of a test machine (i.e., part of an engine) on a partial test bench, it is advantageous to monitor the shaft line corresponding to the mechanical coupling between the partial test bench and the test machine. Test machines (for example compressors) are often driven by electric motors, reduction gears or step up gears and shaft lines belonging to partial test benches. Other machines, for example machines for making partial tests of a gas turbine are also coupled to shaft line systems. Regardless of the test machines used, it is advantageous to monitor bearings supporting the shaft lines.

Furthermore, for a mechanical system 3 composed of a complete engine on a test bench, there is no mechanical coupling between the engine and the bench but it is always advantageous to monitor engine bearings.

Thus according to these examples, the measurements sub-set related to bearings can be selected that may comprise low frequency measurements (for example rotation speeds, pressures, temperatures, etc.) and high frequency measurements (for example vibrations, acoustic waves and accelerations).

Thus, the reception means 11 are configured to receive an endogenic signal representative of endogenic parameter measurements and an exogenic signal representative of exogenic parameter measurements at each instant in successive instants. The exogenic signal is acquired at a predetermined low frequency fs1 (of the order of 1 Hz) and the endogenic signal is acquired at a predetermined high frequency fs2 (of the order of 50 kHz).

The read means 13 are configured to chop endogenic and exogenic signals into packets of endogenic and exogenic time signals respectively, in time at each instant in successive instants. Packets of time signals are sent to the processing means 7. These processing means comprise chopping means 19, calculation means 21 and detection means 23.

The chopping means 19 are configured to chop the passband of packets of endogenic signals into a predetermined sub-set of frequency sub-bands at the same high frequency fs2, at each instant in successive instants. For example, chopping may be done at regular intervals of about 1 ms or 2 ms.

The calculation means are also configured to determine a corresponding estimating signal at each instant in these successive instants and for each frequency sub-band. For example, the estimating signal is a mean value signal or a root mean square (RMS) type signal.

The detection means are configured to receive each estimating signal (for example RMS signal) and corresponding packets of exogenic signals in order to detect every deviation in each estimating signal representing initiating failures of the machine, in iso-context (i.e., standard context) and during successive instants. Advantageously, the detection means are adapted to standardize the estimating signal by eliminating local dependences from the acquisition context thus making it possible to detect any deviation of the estimating signal in iso-context. This deviation reveals initiating failures in the mechanical system.

Figure 2:
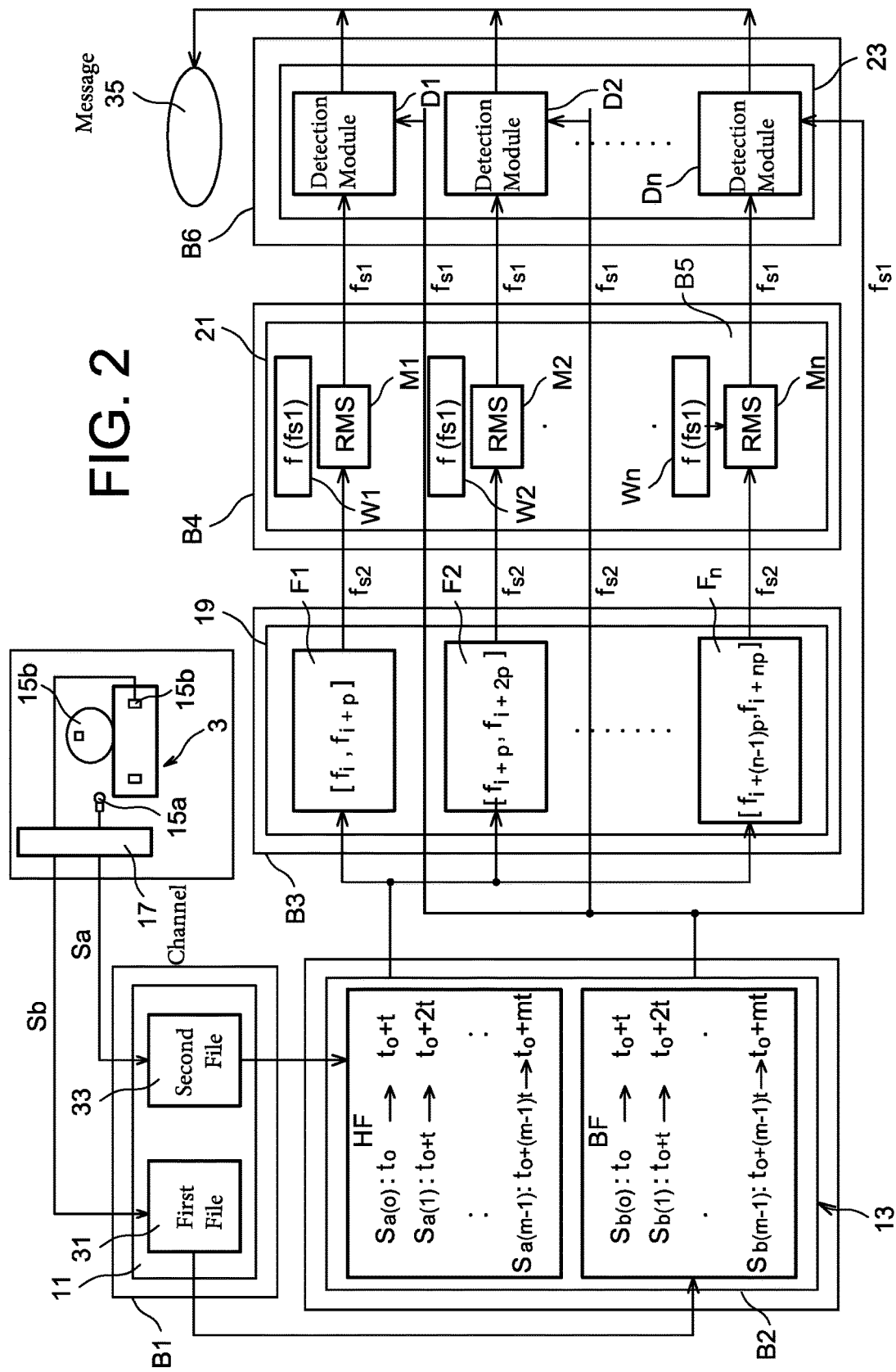
FIG. 2 is a block diagram showing a method of detecting initiating failures in a mechanical system according to a preferred embodiment of the invention.

FIG. 2 shows a block diagram of a method of detecting initiating failures of a mechanical system according to a preferred embodiment of the invention.

In block B1, the reception means 11 are configured to receive analog signals representative of endogenic and exogenic parameter measurements derived from the different sensors 15a, 15b at each instant in successive instants, and to convert them into endogenic and exogenic digital signals respectively. In particular, each endogenic signal $S_a$ is recorded at high frequency fs2 (for example of the order of a few tens of kHz) in a first file 31 and each exogenic signal $S_b$ is recorded at a low frequency fs1 (of the order of a few Hz) in a second file 33.

In block B2, the read means 13 are configured to chop the endogenic HF signal $S_a$ into m portions or packets of time signals $S_{a(0)}, \ldots, S_{a(m-1)}$ in m files (where m is an integer greater than one) at the same high frequency fs2 and the same durations t. Similarly, the LF exogenic signal $S_b$ is chopped into m packets of time signals $S_{b(0)}, \ldots, S_{b(m-1)}$ in m files at the same low frequency fs1 and with the same durations t.

In block B3, the chopping means 19 are configured to chop the passband of endogenic signal packets $S_{a(0)}, \ldots, S_{a(m-1)}$ into a determined set of frequency sub-bands at each instant. The set of frequency sub-bands may be determined by expertise following a compromise criterion between the calculation time and the required precision. The finer the chopping, the higher the precision but on the other hand the calculation speed will be reduced. For example a good compromise for a passband of 20 kHz may be chopping at 1000 Hz or 2000 Hz.

In particular, each endogenic signal packet is passed in n filters F1, ..., Fn (where n is an integer more than one) that chop the passband into n consecutive frequency bands $[f_i, f_{i+p}], [f_{i+2p}], \ldots, [f_{i+(n-1)p}, f_{i+np}]$. Thus, there are n signals in n consecutive frequency bands for each signal portion. For example, a 20 kHz passband may advantageously be chopped into about ten consecutive frequency bands.

In block B4, the calculation means 21 are configured to determine a corresponding estimating signal at each instant in these successive instants and for each frequency sub-band. In particular, the calculation means 21 comprise estimating modules M1, ..., Mn generating an estimating signal for each frequency sub-band. Thus, the estimating modules M1, ..., Mn for example calculate RMS values of HF (High Frequency) signals sampled at fs2.

In block B5, windowing means W1, ..., Wn included in the processing means are configured to under-sample each estimating or RMS signal corresponding to each frequency sub-band at the same sampling frequency as the low frequency fs1 of the exogenic time signals. In particular, windowing with width fs1 configures the estimating module such that the HF signal sampled at fs2 at the output is re-sampled at a low frequency fs1. Windowing can be defined with or without overlap while selecting a number of windows equal to the duration t of the time signal multiplied by the required sampling frequency fs1. Thus configured, the result at the output from each estimating module M1, ..., Mn is an RMS signal under-sampled at fs1 (i.e., at the same sampling frequency as the packets of exogenic low frequency signals) and with the same duration as the corresponding input signal. In block B6, the detection means 23 comprise n detection modules D1, ..., Dn.

Thus, the n estimating signals (for example RMS signals) in n consecutive frequency bands sampled at fs1 and the LF exogenic signal packets sampled at fs1 pass in the n detection modules D1, ..., Dn respectively. The detection modules D1, ..., Dn may for example implement usual behavior models and make normality measurements (or scores) by probability calculations. For example, each detection module can be adapted to detect an abnormal behavior of the endogenic signal monitored in its context relative to a usual behavior of an endogenic signal learned on the fly or after a more or less distant past.

The detection modules D1, ..., Dn may use a technique like that described in the patent application of the applicant FR2965915 or any other technique known in the state of the art.

In particular, each detection module is adapted to detect the deviation of the estimating signal in iso-context, during successive instants. For example, each detection module D1, ..., Dn may be configured to detect the deviation of the RMS level of the estimating signal by calculating a score or a probability of deviation for each RMS signal at each instant among successive instants, depending on the corresponding exogenic time signals. It should be noted that the RMS signal and the corresponding exogenic signals are sampled at the same frequency fs1.

Thus, the input data for each detection module D1, ..., Dn consists of first data to be monitored corresponding to the RMS signal sampled at fs1, associating second data with them corresponding to packets of LF exogenic signals sampled at fs1 describing contextual aspects of current operation. The first and second input data may for example be transformed into exogenic and endogenic indicator vectors respectively, at a current instant. The exogenic indicator vector is used to identify the context or operating mode in which the endogenic indicator vector is defined.

A context may be identified automatically for example by calculating the distances of an exogenic indicating vector at the current instant from exogenic indicator vectors constructed at earlier instants. As a variant, a context may also be identified by analyzing the fact that the current exogenic indicator vector belongs to a set of contexts constructed by learning.

In the case in which a detection module D1, ..., Dn detects initiating failures, the detection device triggers or sends an alert message 35. As a variant, the alert message is only triggered after several successive detections confirming the anomaly or the initiating failure and possibly after corroboration by different detection modules D1, ..., Dn.

Figure 3:
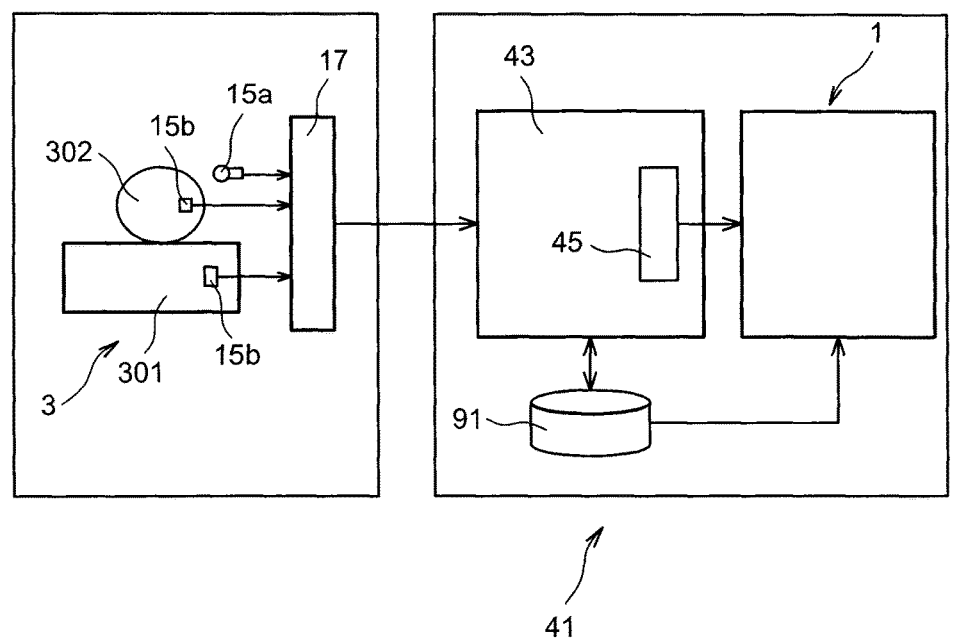
FIG. 3 diagrammatically shows a management device of the mechanical system according to the invention.

FIG. 3 diagrammatically shows a management device of the mechanical system according to the invention.

The management device 41 comprises a test device 43 connected to the mechanical system 3 (for example a test bench 301 and a component of an engine 302) and to the detection device 1. The test device 43 is configured to control the mechanical system 3 and to record data output from sensors 15 in the storage means 91. Furthermore, the detection device 1 is connected to the mechanical system 3 through the test device 43 and through a data bus 45 that sends data output from the mechanical system 3 to it. This configuration does not disturb operation of the mechanical system 3.

For example, the test device 43 may be installed in a first computer and the detection device 1 may be installed in a second computer at a distance from the first.

The invention also relates to a computer software product that could be implemented in the different elements of the detection device, this software comprising code instructions adapted to the use of a method according to the invention as described above.

The invention claimed is:

1. A device for detection of initiating failures in a mechanical system composed of a machine or part of a machine on a test bench, the device comprising:
- an acquisition circuit configured to acquire packets of endogenic and exogenic time signals corresponding to measurements of endogenic and exogenic parameters specific to said mechanical system respectively, at successive instants;
- a chopping circuit configured to chop a passband of said endogenic signal packets into a determined set of frequency sub-bands, at each instant in said successive instants;
- a calculation circuit configured to determine a corresponding estimating signal for each frequency sub-band at each instant in said successive instants; and
- a detection circuit configured to receive each said estimating signal and the corresponding exogenic signal packets during said successive instants, and to detect any deviation in each said estimating signal representing initiating failures of said machine in iso-context.

2. The device according to claim 1, wherein said estimating signal is an RMS (Root Mean Square) signal, in each frequency sub-band.

3. The device according to claim 1, wherein said acquisition circuit is further configured to:
- receive an endogenic signal at each instant in said successive instants, representing measurements of endogenic parameters and an exogenic signal representing measurements of exogenic parameters, said exogenic signal being acquired at a predetermined low frequency (fs1) and said endogenic signal being acquired at a predetermined high frequency (fs2), and
- chop said endogenic and exogenic signals in time into said endogenic and exogenic time signal packets respectively.

4. The device according to claim 1, wherein said chopping circuit comprises a determined set of filters adapted to chop the passband of endogenic signal packets into a set of consecutive frequency sub-bands.

5. The device according to claim 4, wherein the calculation circuit is configured to under-sample each estimating signal corresponding to each frequency sub-band at a same sampling frequency as a low frequency fs1 of exogenic time signals.

6. The device according to claim 5, wherein the detection circuit is configured to calculate a probability of deviation conditioned by the corresponding exogenic time signals for each estimating signal, said estimating signal and said corresponding exogenic signals being sampled at the same said low frequency fs1.

7. The device according to claim 1, wherein said endogenic measurements comprise vibration measurements and/or acoustic measurements, and said exogenic measurements comprise context measurements among the following measurements: pressure measurements, temperature, torque and speed measurements of at least part of the elements of said mechanical system.

8. The device according to claim 1, wherein said machine is an aircraft engine or a component of an aircraft engine.

9. A method of detecting initiating failures in a mechanical system composed of a machine or part of a machine on a test bench, the method comprising:
- acquiring endogenic and exogenic time signal packets at successive instants corresponding to endogenic parameter measurements and exogenic parameter measurements specific to said mechanical system respectively;
- chopping a passband of said endogenic signal packets into a determined set of frequency sub-bands at each instant in said successive instants;
- determining an estimating signal corresponding to each frequency sub-band at each instant in said successive instants;
- receiving each said estimating signal and the corresponding exogenic signal packets during said successive instants; and
- detecting any deviation in each said estimating signal representative of initiating failures of said machine, in iso-context.

* * * * *